United States Patent
Marcoyannopoulou-Fojas

(10) Patent No.: US 6,537,226 B1
(45) Date of Patent: Mar. 25, 2003

(54) DEVICE AND METHOD OF DETERMINING ARTERIAL WALL ELASTICITY

(76) Inventor: Helen Marcoyannopoulou-Fojas, Hridanou 17, Athens 115 28 (GR)

(*) Notice: Subject to any disclaimer, the term of this patent is extended or adjusted under 35 U.S.C. 154(b) by 0 days.

(21) Appl. No.: 09/530,514
(22) PCT Filed: Sep. 6, 1999
(86) PCT No.: PCT/GR99/00032
§ 371 (c)(1),
(2), (4) Date: May 2, 2000
(87) PCT Pub. No.: WO00/13584
PCT Pub. Date: Mar. 16, 2000

(30) Foreign Application Priority Data

Sep. 9, 1998 (GR) .......................... 980100336

(51) Int. Cl.$^7$ ................................................ A61B 5/02
(52) U.S. Cl. ...................................... 600/500; 600/586
(58) Field of Search ................................ 600/516, 586, 600/500

(56) References Cited

U.S. PATENT DOCUMENTS 5,249,467 A * 10/1993 Takashima .................... 73/702

* cited by examiner

Primary Examiner—Kevin Shaver
Assistant Examiner—Patricia Mallari

(57) ABSTRACT

A new and original indirect method of determining arterial wall elasticity is described. The speed of the transmission of the pulse wave between two points in the arterial system, i.e., the left external carotid and left dorsalis pedis arteries, is measured. The faster the transmission of the pulse wave, the less elastic is the arterial wall. The time of the transmission of the pulse wave is measured by recording the arterial pulses in the left external carotid and left dorsalis pedis arteries with a device, which I originally designed and described in detail above, attached to the center of the pick up microphone of a high frequency oscillograph, simultaneously with the Std. Lead II of the ECG. The device produces pulses which very closely resemble the intra arterial pulses and this is essential as said pulses have foot points which are easily distinguishable and marked as reference points for accurate time interval measurements. In this method a longer segment of the arterial system is measured so that the margin of error for statistical analysis is loss. This method is original as the "peripheral artery" used is the left dorsalis pedis artery and this has never been mentioned in the medical literature up to the present. Also, the segment from the left external carotid artery to the left dorsalis pedis artery is an original idea, as the medical literature up to present describes segments from the left external carotid artery to the left femoral artery or from the external carotid artery to the brachial or radial arteries which are shorter segments compared to that of my method.

1 Claim, 3 Drawing Sheets

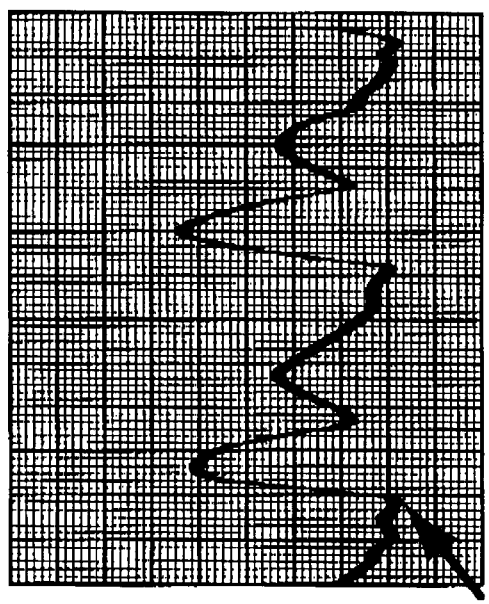
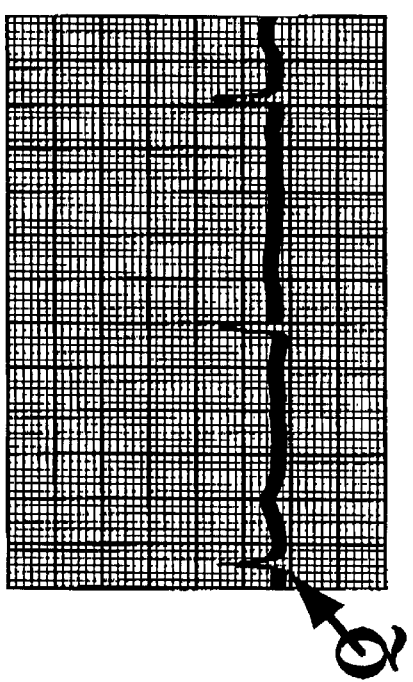
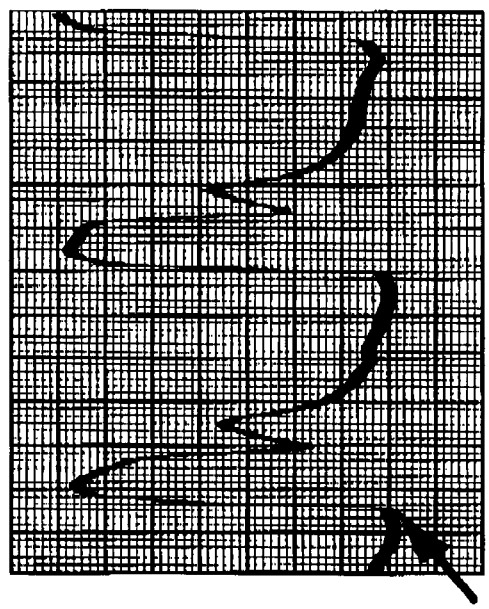
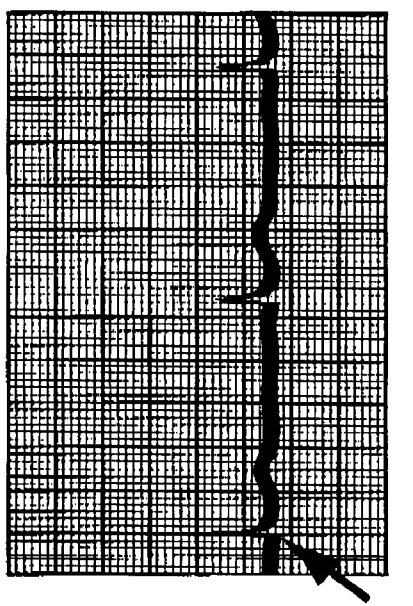
Figure 2

DEVICE AND METHOD OF DETERMINING ARTERIAL WALL ELASTICITY

The present invention relates to medical technology but more particularly, to a device and method of determining the elasticity of the arterial wall.

BACKGROUND OF THE INVENTION

I have been working on the oscillographic method of recording arterial pulses for many years now. When I started doing researches on haemodynamics, particularly pulse wave velocity, for which I was granted a Fellowship by the International Federation of University Women, I was confronted with the problem of recording arterial pulses which resembled the intra arterial pulses as closely as possible. This was essential as these said pulses showed the foot points or starting points of the recorded pulses which serve as reference points and which are marked for time interval measurements. After many repeated trials, I was able to design an attachment to the pickup microphone of the NEP pulse recording unit (Type A-643) of Sanborn. This attachment enabled me to record the desired pulses described above so that I was able to continue with my researches on pulse wave velocity. Said attachment is described in detail below.

In determining the elasticity of the arterial wall indirectly by measuring the time of the transmission of the pulse wave through the arteries, we use a "central artery" and a "peripheral artery" as reference points. The time interval between the instant the pulse is recorded in the "central artery" and the instant that the same pulse is recorded in the "peripheral artery", is a measure of the time delay between the two reference points. In the medical literature, the left external carotid artery has always been used as the "central artery" and the left femoral, brachial, radial or other arteries have been used as the "peripheral artery". The use of the left dorsalis pedis artery as a "peripheral artery" has never been mentioned in the medical literature up to the present. It was my original idea to make use of the dorsalis pedis artery as the "peripheral artery" on the assumption that I will be measuring a longer segment of the arterial system so that the margin of error for statistical analysis is less. Also, this artery is well exposed and easy to locate so that the sensor can be placed over it with ease.

Compared to other non invasive methods of measuring the pulse wave velocity (Doppler flow, ultrasounds and magnetic resonance) my device and method are simple, easy and fast to perform, reproducible, relatively inexpensive, compact and portable so that it is very suitable for epidemiologic studies in large populations especially in developing countries.

BRIEF SUMMARY OF THE INVENTION

The primary object of this invention is to introduce a new device and an original method which has never been described in the medical literature for indirectly determining the elasticity of the arterial wall on a living subject.

The left external carotid artery as the "central artery" has been described by many authors, but the use of the left dorsalis pedis artery as the "peripheral artery" is my original idea and has not been mentioned in the medical literature up to the present. These arteries are well exposed, easily located and the distance between them is much longer compared to other methods heretofore described. The longer segment measured makes the margin or error for statistical analysis less, The subjects used for these studies are within a specific height range.

It is essential that the pulses recorded resemble as closely as possible the intra arterial pulse so that the foot points are clearly distinguishable as they are marked and used as reference points for time interval measurements. This has been achieved by using a special device that I have originally designed to be attached to the pick up microphone of the high frequency oscillograph. Specifically, the device is a circular metallic plate, one centimeter in diameter and one millimeter thick whose center is welded to the center of the pick up microphone with a solid tubular rod, one centimeter long and one millimeter in diameter. This device is placed on the skin over the artery. The anacrotic pulses recorded distinctly shows the foot points which serve as reference points in measuring the distances between the pulses of the left external carotid ("central artery") and left dorsalis pedis ("peripheral artery").

BRIEF DESCRIPTION OF FIGURES

FIG. 2 shows the left external carotid pulse and left dorsalis pedis pulse recorded simultaneously with the STD Lead II of the ECG.

DETAILED DESCRIPTION OF THE INVENTION

Figure 1:
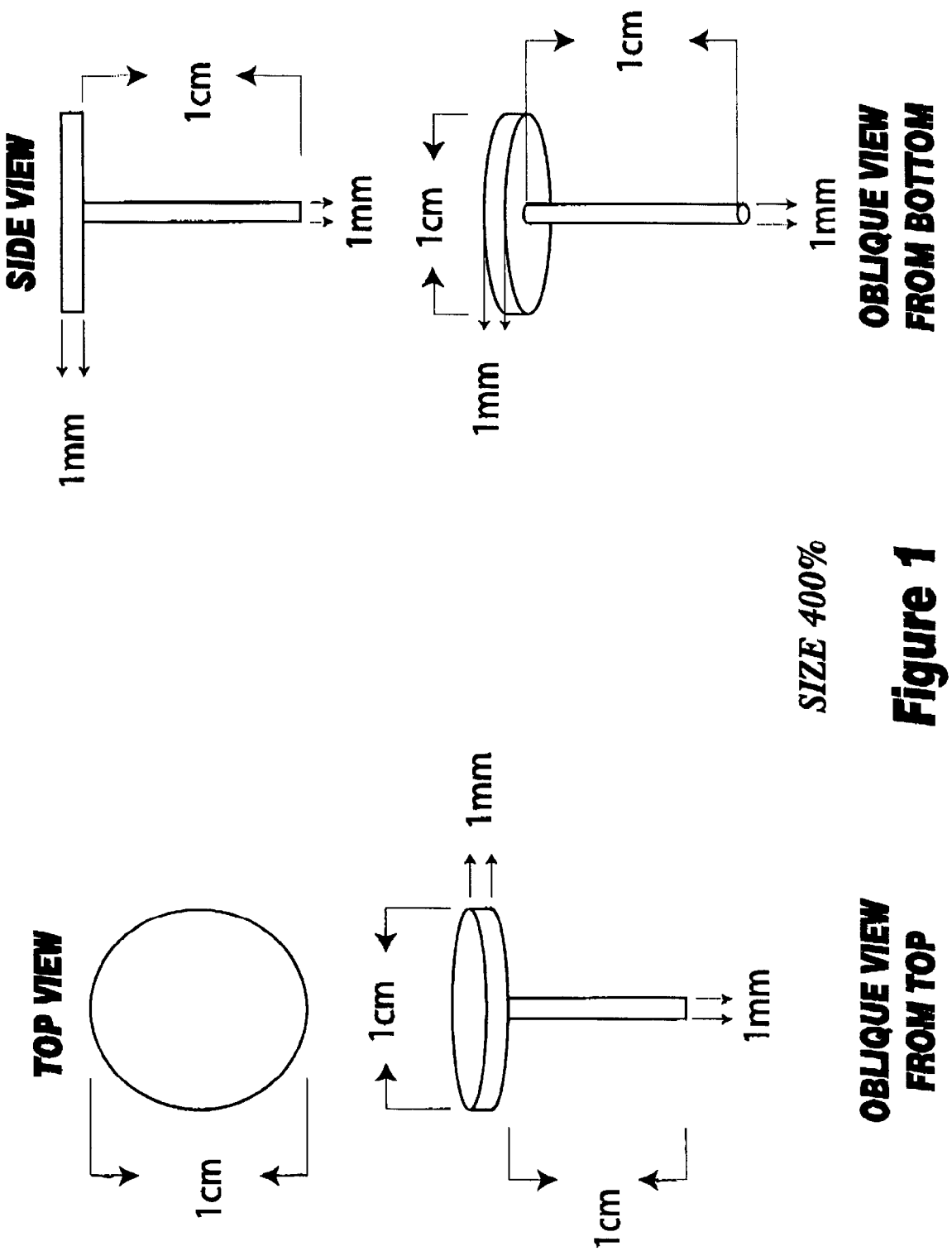
FIG. 1 is a perspective view of the device used in the invention.
Figure 3:
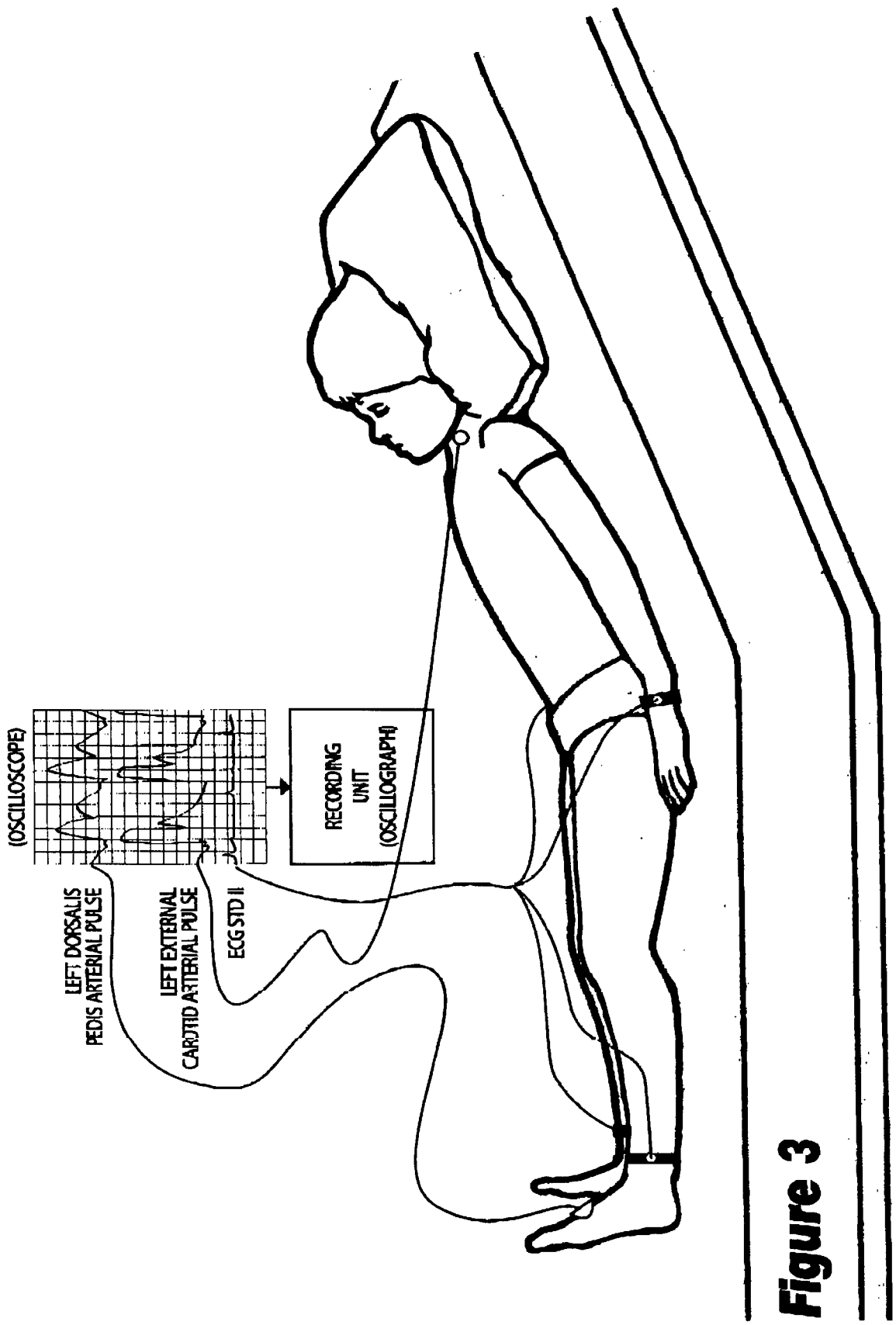
FIG. 3 is a schematic figure of a subject in the semi recumbent position with the sensors for the arterial pulses and electrodes for the ECG in their proper places and connected to the oscilloscope and Oscillograph.

As shown in FIG. 1, the device is a circular metallic plate one centimeter in diameter and one millimeter thick in the center of which is a solid tubular metallic rod one centimeter long and one millimeter in diameter whose free end is welded to the center of the pick up microphone of the NEP Pulse Recording Unit (Type-643) of Sanborn. With this attachment device placed on the skin directly over the arteries, pulses of the left external carotid and left dorsalis pedis arteries are obtained as shown in FIG. 2. FIG. 3 shows a subject in the semi recumbent position in a room with temperature controlled as constantly as possible and the sensors placed over the left external carotid and left dorsalis pedis artcrics. These pulses are recorded simultaneously with the STD Lead II of the ECG (FIG. 2). Recordings were made in some subjects at intervals of six, twelve and eighteen months and the results were the same. Referring to FIG. 2, Q is the start of the isometric ventricular contraction, A is the foot point of the anacrotic pulse of the left external carotid artery and A-1 is the foot point of the anacrotic pulse of the left dorsalis pedis artery. The time interval QA is the time the pulse travels from the left ventricle to the left external carotid artery point and the time interval QA-1 is the time the pulse travels from the left ventricle to the left dorsalis pedis artery point. Therefore, the difference between the time intervals QA-1 and QA is a measure of the time delay between the instant the pulse is recorded from the "central artery", i.e., the left external carotid artery and the instant that the pulse is recorded from the "peripheral artery", i.e., the left dorsalis pedis artery. This method is non invasive, simple, easy and fast to perform, reproducible and relatively inexpensive. Its results are similar to more sophis ticated and expensive methods. It is very applicable for mass screening of big populations (normals and high risk individuals) especially in developing countries.

I claim:

1. A new and original non-invasive method of indirectly determining the elasticity of the arterial wall in a subject which has not been mentioned in the medical literature up to present comprising the steps of:
   a) making use of a patient's left external carotid artery as a "central artery" and the patient's left dorsalis pedis as a "peripheral artery";
   b) attaching a metallic plate on a pick-up microphone of a high frequency oscillograph;
   c) placing the metallic plate directly on the patient's skin over the left external carotid artery and the left dorsalis pedis;
   d) recording arterial pulses of the left external carotid and the left dorsalis pedis arteries using the oscillograph for a period of time; and
   e) getting a difference between the arterial pulses to measure a time interval between the instant that the pulse is recorded from the "central artery" and the instant that the same pulse is recorded from the "peripheral artery".

* * * * *